(12) United States Patent
Lefkov et al.

(10) Patent No.: US 7,970,462 B2
(45) Date of Patent: Jun. 28, 2011

(54) IMPLANTABLE MEDICAL DEVICES EVALUATING THORAX IMPEDANCE

(75) Inventors: Sharon Lefkov, Portland, OR (US); David F. Hastings, Lake Oswego, OR (US); Christopher S. de Voir, Tigard, OR (US); Garth Garner, Tigard, OR (US); Dirk Muessig, West Linn, OR (US); Hannes Kraetschmer, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 967 days.

(21) Appl. No.: 11/754,973

(22) Filed: May 29, 2007

(65) Prior Publication Data

US 2008/0300504 A1   Dec. 4, 2008

(51) Int. Cl.
    *A61B 5/02*   (2006.01)
    *A61B 5/08*   (2006.01)
    *A61B 5/05*   (2006.01)
    *A61N 1/00*   (2006.01)

(52) U.S. Cl. ........ 600/547; 600/484; 600/485; 600/486; 600/506; 600/538; 607/2; 607/18

(58) Field of Classification Search .................. 600/547, 600/509, 529, 484, 485, 486, 506, 538; 607/4, 607/17, 2, 28, 509, 529, 18
    See application file for complete search history.

(56) References Cited

U.S. PATENT DOCUMENTS

| 2,820,418 | A | * | 1/1958 | Sullivan et al. | 417/198 |
| 5,174,286 | A | * | 12/1992 | Chirife | 607/11 |
| 5,562,711 | A | | 10/1996 | Yerich | |
| 5,876,353 | A | | 3/1999 | Riff | |
| 5,957,861 | A | | 9/1999 | Combs | |
| 6,473,640 | B1 | | 10/2002 | Erlebacher | |
| 6,512,949 | B1 | * | 1/2003 | Combs et al. | 600/547 |
| 6,512,952 | B2 | * | 1/2003 | Stahmann et al. | 607/9 |
| 6,628,988 | B2 | * | 9/2003 | Kramer et al. | 607/9 |

(Continued)

FOREIGN PATENT DOCUMENTS

EP        0310026        4/1989

(Continued)

OTHER PUBLICATIONS

European Search Report (Attached).

*Primary Examiner* — Max Hindenburg
*Assistant Examiner* — Sean P Dougherty
(74) *Attorney, Agent, or Firm* — Arc IP Law, PC; Joseph J. Mayo

(57) ABSTRACT

Implantable medical device with an impedance determination unit with constant current/voltage source having current feed terminals connected to electrodes for intracorporal placement which generates measuring current pulses having constant current/voltage, for causing a current through a body via intracorporally placed electrodes, a measuring unit for measuring voltage/current strength of voltage/current fed through body, an impedance value determination unit connected to the current/voltage source and adapted to determine an impedance value for each measuring current pulse, and an impedance measuring control and evaluation unit connected to the impedance determination unit which controls the unit and evaluates a sequence of consecutive impedance values, the impedance determination unit further adapted to determine at least intrathoracic and intracardiac impedance values for same period of time, the intrathoracic values sampled with a lower sampling rate than the intracardiac values.

31 Claims, 7 Drawing Sheets

U.S. PATENT DOCUMENTS

| | | | |
|---|---|---|---|
| 6,643,546 B2 * | 11/2003 | Mathis et al. | 607/9 |
| 7,200,442 B1 | 4/2007 | Koh | |
| 7,308,311 B2 * | 12/2007 | Sorensen et al. | 607/32 |
| 7,340,296 B2 * | 3/2008 | Stahmann et al. | 600/547 |
| 7,630,763 B2 * | 12/2009 | Kwok et al. | 607/6 |
| 7,899,522 B1 * | 3/2011 | Koh et al. | 600/513 |
| 2003/0023184 A1 | 1/2003 | Pitts-Crick | |
| 2003/0120164 A1 * | 6/2003 | Nielsen et al. | 600/513 |
| 2003/0204213 A1 | 10/2003 | Jensen | |
| 2004/0102712 A1 * | 5/2004 | Belalcazar et al. | 600/547 |
| 2004/0102721 A1 * | 5/2004 | McKinley | 600/587 |
| 2004/0220632 A1 * | 11/2004 | Burnes | 607/9 |
| 2005/0080460 A1 | 4/2005 | Wang | |
| 2005/0090753 A1 * | 4/2005 | Goor et al. | 600/508 |
| 2005/0109338 A1 * | 5/2005 | Stahmann et al. | 128/204.18 |
| 2005/0124900 A1 * | 6/2005 | Stadler et al. | 600/509 |
| 2005/0182447 A1 | 8/2005 | Schecter | |
| 2005/0216067 A1 * | 9/2005 | Min et al. | 607/17 |
| 2006/0184060 A1 * | 8/2006 | Belalcazar et al. | 600/547 |
| 2006/0258952 A1 * | 11/2006 | Stahmann et al. | 600/547 |
| 2006/0293609 A1 * | 12/2006 | Stahmann et al. | 600/547 |
| 2007/0088220 A1 * | 4/2007 | Stahmann | 600/485 |
| 2007/0142733 A1 * | 6/2007 | Hatlestad et al. | 600/508 |
| 2007/0239054 A1 * | 10/2007 | Giftakis et al. | 600/513 |
| 2008/0091114 A1 * | 4/2008 | Min et al. | 600/508 |
| 2008/0190430 A1 * | 8/2008 | Melker et al. | 128/204.23 |
| 2008/0194998 A1 * | 8/2008 | Holmstrom et al. | 600/595 |
| 2008/0243025 A1 * | 10/2008 | Holmstrom et al. | 600/547 |
| 2009/0099475 A1 * | 4/2009 | Bjorling | 600/547 |
| 2010/0113961 A1 * | 5/2010 | Ohlander et al. | 600/547 |

FOREIGN PATENT DOCUMENTS

| | | |
|---|---|---|
| WO | WO9819737 | 5/1998 |

* cited by examiner

IMPLANTABLE MEDICAL DEVICES EVALUATING THORAX IMPEDANCE

BACKGROUND OF THE INVENTION

1. Field of the Invention

The invention refers to implantable medical devices (IMDs) providing means for determining and evaluating thoracic impedance. The preferred embodiment relates in particular to implantable cardiac pacemakers, cardiac resynchronization therapy devices, transplant rejection monitoring devices, or implantable cardioverter/defibrillators (ICD).

2. Description of the Related Art

This invention relates to an implantable medical device and a method of assessing pulmonary congestion usually associated with worsening heart failure. Heart failure (HF) can cause a build up of fluid in the lungs and body of a patient. Such an increase of fluid in the lungs can be determined by impedance monitoring as is, for example, disclosed in U.S. Pat. No. 5,876,353, U.S. Pat. No. 5,957,861 and U.S. Pat. No. 6,473,640.

BRIEF SUMMARY OF THE INVENTION

It is an object of the invention to provide an implantable medical device that provides health care personnel with periodic information on the pulmonary and cardiovascular status of the patient and timely alerts of adverse changes in said status.

According to the present invention, the objective of the invention is achieved by an implantable medical device featuring an impedance determination unit and an impedance measuring control and evaluation unit. The impedance determination unit comprises a constant-current (voltage) source or a constant-voltage (current) source, a measuring unit and an impedance value determination unit (hereinafter, 'current unit' shall refer to either). Basically, the current unit generates voltage or current pulses (hereinafter, referred to as 'forcing function') that are injected into a patient's body via electrodes. The measuring unit measures either a voltage or a current strength (response function) induced by the current unit. The impedance value determination unit is connected with the current unit and the measuring unit and is adapted to determine an impedance value for each response function generated by the forcing function.

The impedance measuring control and evaluation unit is connected to the impedance determination unit and is adapted to control the impedance determination unit in order to receive a sequence of consecutive impedance values and to evaluate such sequence of consecutive impedance values received from the impedance determination unit. Further, the impedance determination unit determines at least an intrathoracic impedance and an intracardiac impedance wherein the intrathoracic impedance is measured between a case of the implantable medical device and an intracardiac electrode and the intracardiac impedance is measured between the left and right ventricles of the heart. Preferably, at least two different kinds of intrathoracic impedance values are measured, a first kind being measured between the implantable medical devices case and a right ventricular electrode and the second kind of intrathoracic impedance values are measured between the implantable medical devices case and a left ventricular electrode.

Preferably, the intrathoracic impedance values are sampled with a lower sampling rate than the intracardiac impedance values. For example, adequate band width for the intrathoracic impedance values would be about 2.5 Hz. Oversampling at 32 Hz followed by low-pass filtering down to 2.5 Hz is also suitable for intrathoracic impedance. On the other hand, the adequate band width for the intracardiac impedance would be about 40 Hz requiring sampling at 80 Hz. Here oversampling at 128 Hz and low-pass filtering down to 40 Hz is suitable.

The forcing function for intrathoracic impedance measurement preferably is sourced via the right ventricular or a left ventricular ring electrode and the current sink would be the implantable medical device's case. Measurement of the response function preferably is carried out between a right ventricular tip-electrode and the implantable medical device's case or a left ventricular tip-electrode and the implantable medical device's case.

For intracardiac impedance measurements, injecting a forcing function from a right ventricular ring electrode to a right ventricular tip-electrode and measuring a response function between a left ventricular ring electrode and a left ventricular tip-electrode is preferred.

Further possible electrode configurations for application of the forcing function and measurement of the response function become apparent from the following table 1.

TABLE 1

Configurations for thoracic fluid status monitoring.

| Diagnostic Value | Polarity | Forcing contacts | Response contacts |
|---|---|---|---|
| Primary | Tripolar | RV Ring to Case | RV Tip to Case |
| Primary | Tripolar | LV Ring to Case | LV Tip to Case |
| Primary | Bipolar | RV Coil to Case | RV Coil to Case |
| Primary | Bipolar | LV Coil to Case | LV Coil to Case |
| Secondary | Quadrapolar #1 | LV Ring to RV Ring | LV Tip to RV Tip |
| Secondary | Quadrapolar #2 | RV Ring to RV Tip | LV Ring to LV Tip |
| Secondary | Tripolar | RV Ring to LV Ring | RV Tip to LV Ring |
| Secondary | Tripolar | RV Ring to LV Tip | RV Tip to LV Tip |
| Secondary | Tripolar | LV Ring to RV Ring | LV Tip to RV Ring |
| Secondary | Tripolar | LV Ring to RV Tip | LV Tip to RV Tip |
| Secondary | Bipolar | RV Ring to LV Ring | RV Ring to LV Ring |
| Secondary | Bipolar | RV Tip to LV Tip | RV Tip to LV Tip |
| Secondary | Bipolar | RV Ring to LV Tip | RV Ring to LV Tip |
| Secondary | Bipolar | RV Tip to LV Ring | RV Tip to LV Ring |

In order to realize a variety of possible electrode configurations, preferably a switch matrix is arranged between the electrodes and the current unit and the measuring unit.

Further, it is preferred that the implantable medical device provides an activity sensor such as an accelerometer for assessing a patient's activity level that indicates sleep/wake cycles. The information generated by the activity sensor is fed into the impedance measuring control and evaluation unit in order to enable the impedance measurement control and evaluation unit to consider the activity signal when evaluating the impedance values.

In addition to the electrode configurations listed in table 1 in a preferred embodiment also a $Z_{cardiac}$ waveform from an atrial lead is measured and used to verify the atrial contribution to cardiac output (5% . . . 20%) as an indicator of overall cardiac output and thereby to predict or confirm a contributory cause to lung edema.

With respect to any impedance measurement it is preferred that the implantable medical device's impedance determination unit is adapted to automatically adjust the measurement gains to accommodate values outside the operating range of a quantizer. The gain adjustment process is bidirectional and can adapt to large and small signals. Preferably, variance is used to compute a resolution of a sample average (as opposed to the impedance measurement resolution). The forcing function is adjusted to make the resolution of the average value meet requirements for a test of statistical significance. Because the variance is calculated like the average, the statistical resolution can be estimated due to the relation var/N and subsequently trigger changes to the current value to meet measurement resolution requirements. Overflow restarts a measurement, whereas increases in gain or current are applied to the next measurement.

FURTHER IMPROVED EMBODIMENTS

The impedance measurement control and evaluation unit is further adapted to determine a respiration rate based on the intrathoracic impedance values (specifically, from the respiratory modulation of the cardiac impedance signal—which differentiates from related art which is just a low pass filtering of the impedance signal). The respiration rate then could also be used by the impedance measurement control and evaluation unit to further evaluate the impedance values.

Additionally or alternatively, the impedance measurement control and evaluation unit can be adapted to process a heart rate signal when evaluating the impedance values. The heart rate signal could be derived from the intracardiac impedance values or could be generated by a separate heart rate detector that is connected to sensing means for sensing electric potentials that occur when the myocardium (heart tissue) is excited.

With respect to impedance value evaluation, it is preferred that the measuring control and evaluation unit is adapted to perform a population analysis based on sequences of consecutive impedance values by determining inherent population properties of the measured values. Preferably, this is formed by discriminating clusters of points in a parameter space of at least one and preferably more dimensions, that is, a first dimension is given by a heart rate, and a second dimension is given by an impedance, and the third dimension is either a time of day or a respiratory rate. In the latter case, each point of a cluster is determined by a triplet of values including a heart rate value, an impedance value and either a time of day value or a respiratory rate value that all belong together, that is, they are acquired at least nearly at the same point of time.

Further, the impedance measurement control and evaluation unit is adapted to detect an increase or a decrease in thoracic fluid, and an increased end-systolic volume or a decreased end-systolic volume or a ventricular hypertrophy according to the table 2 below:

pling rate may vary by 10% or less between the pulses. Thus, discrimination between the impedance of different tissue types can be accomplished. In particular, discrimination between the impedance of visceral versus pleural and vascular versus interstitial may be accomplished.

With respect to possible gating of impedance measurement, it is preferred that each sequence of impedance values is gated such that it represents a single full respiratory cycle. Thus, a bias due to measuring impedance values over a partially complete respiration cycle is avoided. This is accomplished by gating the impedance measurement on a true respiratory feature (specifically, one of trough, inhale, peak, or exhale—which differentiates from related art in which any mention of these features referred to the output of the low pass filter and are an artifact of the filter group delay by design).

It is further preferred, that the impedance determination unit or the impedance measurement control and evaluating unit is adapted to initiate recording of sequences of impedance values several times a day, preferably about once an hour.

The implantable medical device (IMD) preferably is a bi-ventricular pacemaker, or a bi-ventricular cardioverter/defibrillator, or a combination of both for example.

A preferred method of measuring and evaluating intrathoracic and intracardiac impedance for monitoring intrathoracic fluid content comprises the steps of:

Continually measuring intrathoracic impedance between a first electrode and a second electrode without regard to the cardiac cycle, achieving reduced amount of electrical noise through the use of filtering, averaging, auto gain, auto current magnitude methods and providing an impedance output signal thereof;

storing the unfiltered impedance output signal for the purpose of incremental or deferred processing, including, but not limited to filtering, averaging, auto gain, auto current magnitude methods, providing an impedance or other synthesized signal thereof for analysis;

performing steps for a predetermined number of measurement unit sample timing ticks to thereby generate a set of unfiltered impedance data; and mathematically manipulating the sample of impedance data to render an estimate of population statistics or a synthesized signal from said sample of impedance data.

TABLE 2

Key indications for thoracic fluid status.

| Diagnostic Value | Indicator | Forcing contacts | Response contacts |
| --- | --- | --- | --- |
| Increased Thoracic Fluid | $Z_{reference} > Z_{recent}$ | RV Ring to Case | RV Tip to Case |
| Increased Thoracic Fluid | $Z_{reference} > Z_{recent}$ | LV Ring to Case | LV Tip to Case |
| Decreased Thoracic Fluid | $Z_{reference} < Z_{recent}$ | RV Ring to Case | RV Tip to Case |
| Decreased Thoracic Fluid | $Z_{reference} < Z_{recent}$ | LV Ring to Case | LV Tip to Case |
| Ventricular Hypertrophy | $Z_{reference} < Z_{recent}$ | LV Ring to RV Ring | LV Tip to RV Tip |
| Increased End-Systolic Volume | $Z_{reference} > Z_{recent}$ | RV Ring to RV Tip | LV Ring to LV Tip |
| Decreased End-Systolic Volume | $Z_{reference} < Z_{recent}$ | RV Ring to RV Tip | LV Ring to LV Tip |

With respect to the forcing function used for the impedance measurements, it is preferred that each current unit pulse is a monophasic pulse, the polarity of which is alternated from pulse to pulse. Further, it is preferred that the pulse width (pulse duration) of the measuring current pulses is modulated such that the pulse width will change from pulse to pulse. Further, inter-pulse delays can be altered and even the sam- It is to be appreciated that features of preferred embodiments of the invention may be combined in any useful manner thus arriving at further preferred embodiments of the invention not explicitly mentioned in this disclosure.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
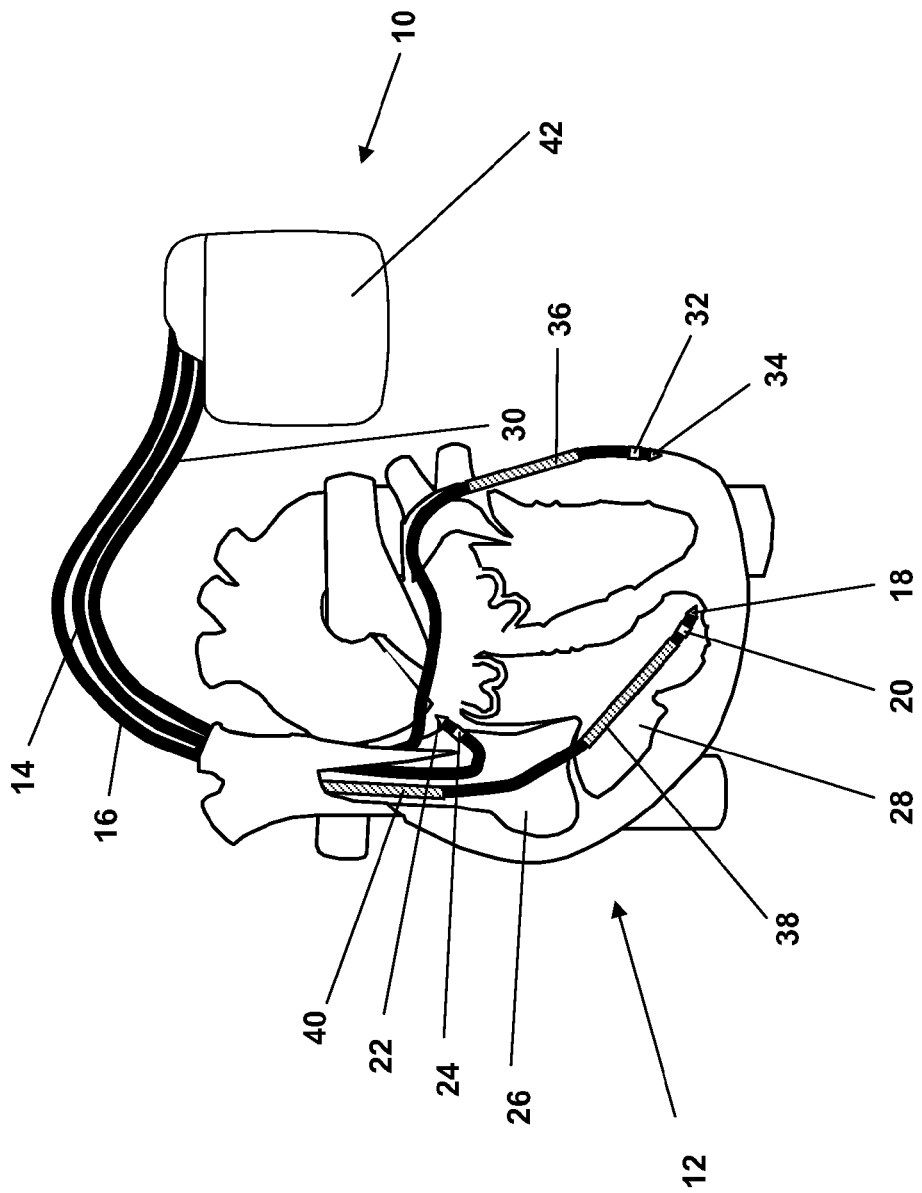
FIG. 1 shows an implantable medical device (in this particular case a bi-ventricular, three chamber pacemaker and defibrillator/cardioverter connected) connected to leads placed in a heart.

In FIG. 1 the implantable medical device is a three chamber biventricular pacemaker and cardioverter/defibrillator 10 that is connected to pacing/sensing leads placed in a heart 12 is illustrated.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation an sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip-electrodes at the very distal end of leads 14 and 16, respectively. Electrode 22 is a right atrial tip electrode RA-Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA-Ring and electrode 20 forms a right ventricular ring electrode RV-Ring. Atrial cardioversion shock coil 40 is coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV-RING 32 a left ventricular tip electrode LV-TIP 34. Further, a left ventricular defibrillation shock coil 36 is arranged on lead 30.

Implantable medical device 10 has a case 42 made from electrically conductive material such as titanium that can serve as a large surface electrode IMD-CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 3:
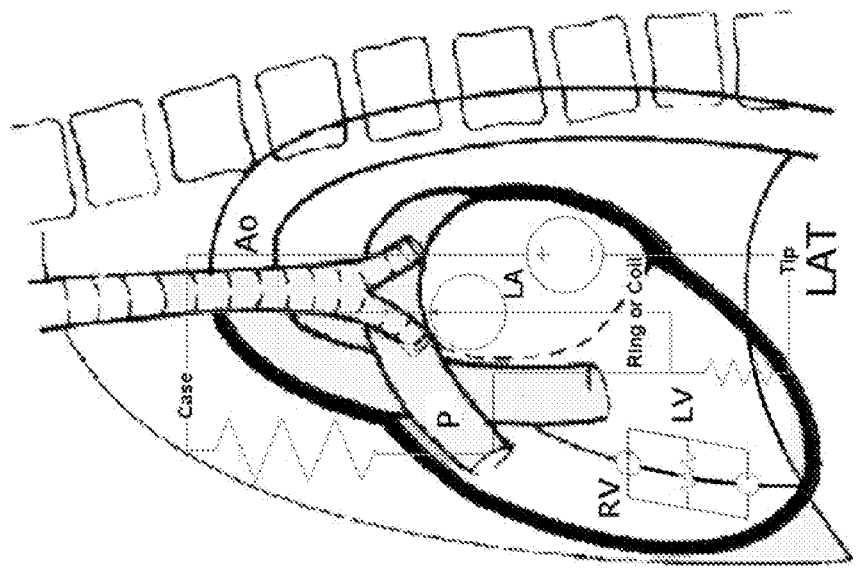
FIG. 3 is a schematic illustration of the measurement paths of another two thoracic fluid status impedance measurement configurations of FIG. 2 in a lateral (LAT) view.
Figure 2:
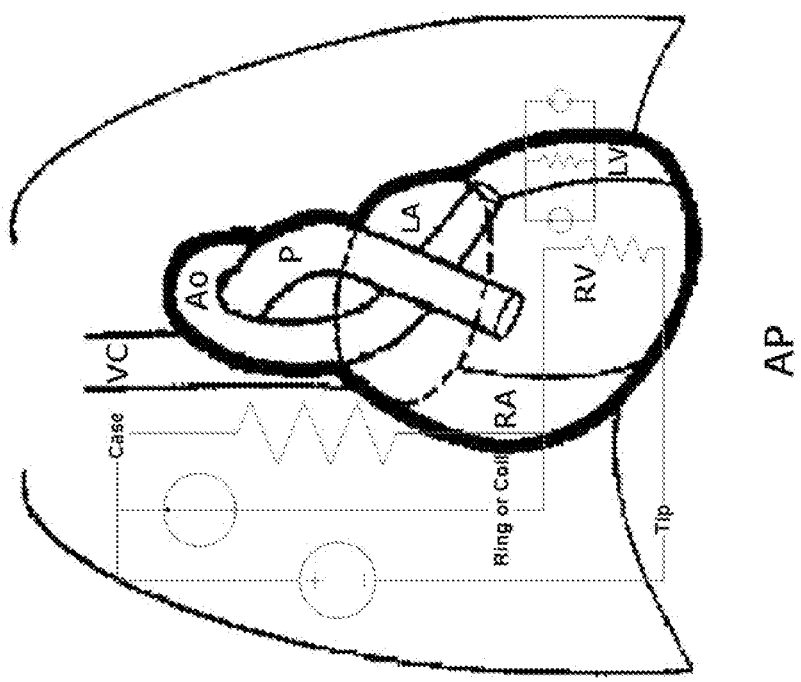
FIG. 2 is a schematic illustration of the measurement paths two thoracic fluids status impedance measurement configurations in an anterior-posterior (AP) view.

A subset of configurations possible (enumerated in Table 1) with the device in FIG. 1, are the preferred configurations illustrated conceptually in FIGS. 2 and 3.

Each impedance measurement configuration has electrodes for the source of the forcing function, electrodes to sense the response function, and an impeding path through fluid and tissue of the thorax. There are two tripolar and two quadrapolar impedance measurement electrode configurations shown. The tripolar impedance measurement electrode configurations shown (in FIGS. 2 and 3) include the case 42 (from FIG. 1) as a common contact element and the impedance path through the thorax between the case 42, and ring and tip electrodes in the heart. The quadrapolar impedance measurement electrode configurations shown here are oriented around the right and left ventricle. In the anterior posterior (AP) view (FIG. 2) the configuration that spans the LV axis, and therefore its fluid volume. In the lateral view (FIG. 3), the configuration axis spans the space from the ventricular septum to the left ventricular free wall emphasizing LV contractility.

Together these configurations can be used to indicate:
a) Primary thoracic fluid change
b) Secondary thoracic fluid change
c) Add confidence to a primary indicator with a secondary indicator.

Although the implantable medical device uses these four configurations in the preferred embodiment, additional configurations are possible as the capabilities of implantable medical devices, such as, pacemakers and ICDs, allow.

Table 1 (see above) shows impedance measurement configurations possible for thoracic fluid status monitoring. Each configuration has a tissue/fluid mass that it emphasizes. For primary diagnostic value, the emphasis includes the lung space. For secondary diagnostic value, the emphasis is on the heart's ability to function as a systolic pump. The details for energetic pathways for three possible configurations for applying the forcing function and sensing the response function are given: Bipolar, Tripolar, and Quadrapolar. It is found that a combination of configurations, such as, a primary RV tripolar measurement configuration whose axis passes through the lung, and a secondary intercardiac configuration provides confirmatory indications of impending or existing elevated pulmonary capillary hydrostatic pressure secondary to heart failure.

Figure 4:
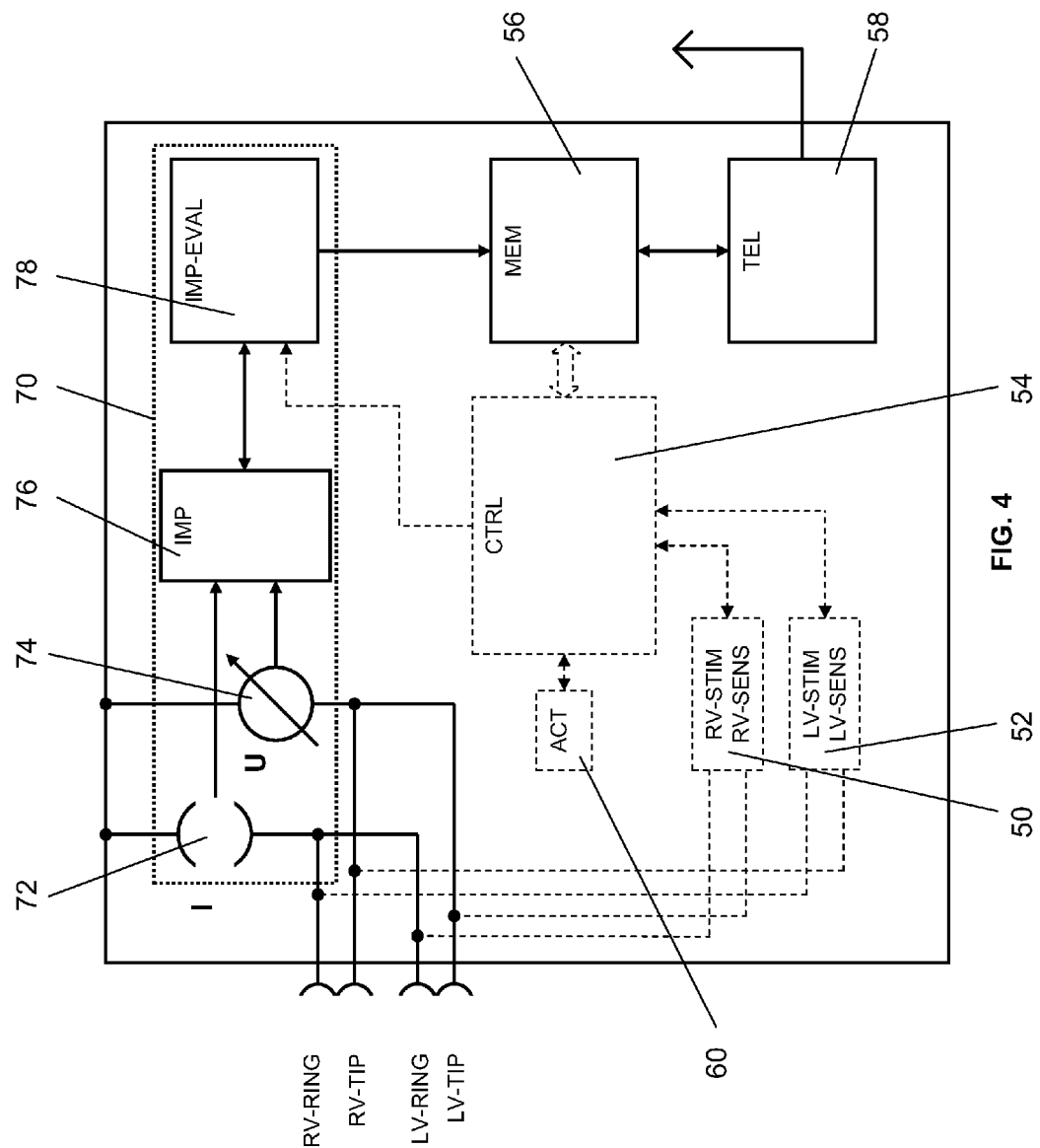
FIG. 4 is a schematic block diagram of one configuration of the device of FIG. 1. For simplicity, the atrial sensing and stimulation channels are omitted.
Figure 5:
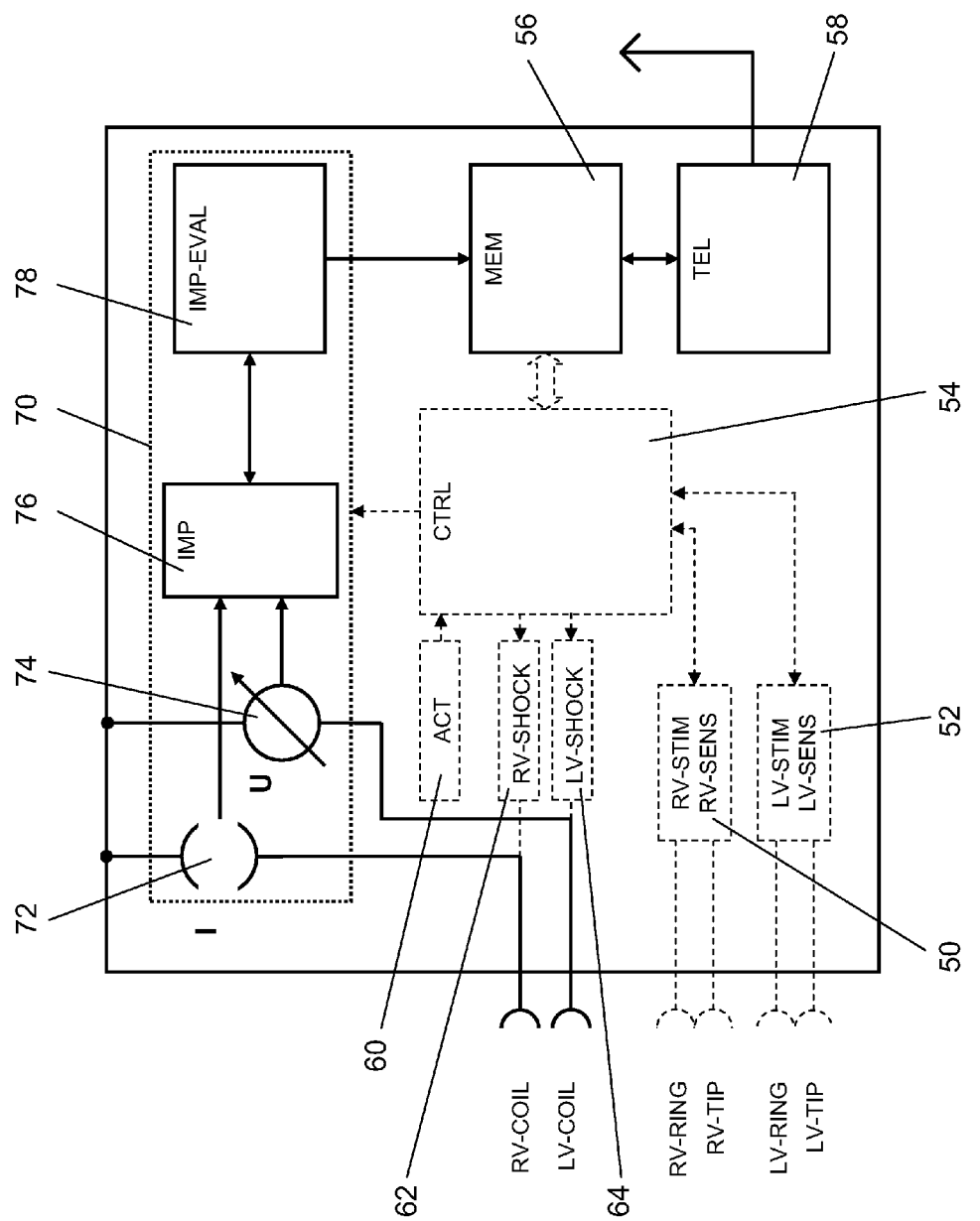
FIG. 5 is a schematic block diagram of a second configuration of the device of FIG. 1.

FIGS. 4 and 5 illustrate simplified block diagrams of an implantable medical device, for example, the one shown as item 10 in FIG. 1. During operation of the implantable medical device leads 16 and 30 (of FIG. 1) are connected to respective output/input terminals RV-RING, RV-TIP, LV-RING and LV-TIP, items 20, 18, 32, and 34, respectively, of implantable medical device 10 as indicated in FIG. 1. For pacing the right and the left ventricle they carry stimulating pulses to the tip electrodes 18 and 34 from an left ventricular stimulation pulse generator LV-STIM 50 and a right ventricular stimulation pulse generator RV-STIM 52, respectively. Further, electrical signals from the right ventricle are carried from the electrode pair 18 and 20, through the lead 16, to the input terminal of right-ventricular sensing stage RV-SENS 50; and electrical signals from the left ventricle are carried from the electrode pair 32 and 34, through the lead 30, to the input terminal of a left ventricular sensing stage LV-SENS 52.

As indicated in FIG. 5, if the implantable medical device is a cardioverter/defibrillator, right ventricular and left ventricular shock generators RV-SHOCK 62 and LV-SHOCK 64 can be provided. Right ventricular and left ventricular shock generators are connected to right ventricular and left ventricular shock coils 38 and 36, respectively.

Controlling the implantable medical device 10 is a control unit CTRL 54 that is connected to stimulation pulse generators/sensing stages RV-STIM/RV-SENS 50 and LV-STIM/LV-SENS 52 as well as right ventricular and left ventricular shock generators RV-SHOCK 62 and LV-SHOCK 64.

Control unit CTRL 54 receives the output signals from the right ventricular sensing stage RV-SENS 50 and from the left ventricular sensing stage LV-SENS 52. The output signals of sensing stages A-SENS 36 and V-SENS 38 are generated each time an R-wave representing an intrinsic ventricular event in the respective ventricle is sensed within the heart 12. Thus, control unit is capable to detect excitations of the myocardium indicating a ventricular contraction and to act as heart rate detector for determination of a heart rate.

Control unit CTRL 54 also generates trigger signals that are sent to the right ventricular stimulation pulse generator RV-STIM 50 and the left ventricular stimulation pulse generator LV-STIM 52, respectively. Control unit CTRL 54 comprises circuitry for timing ventricular (atrial stimulation pulses are also possible but not shown in FIGS. 4 and 5) according to an adequate stimulation rate that can be adapted to a patient's hemodynamic need as pointed out below. Further CTRL 54 can trigger a respective defibrillation shock generator (see FIG. 5) RV-SHOCK 62 and/or LV-SHOCK 64 to generate ventricular or atrial defibrillation shocks if needed.

Still referring to FIGS. 4 and 5, the implantable medical device 10 includes a memory circuit MEM 56 that is coupled to the control unit CTRL 54 over a suitable data/address bus. This memory circuit MEM 58 allows certain control parameters, used by the control unit CTRL 54 in controlling the operation of the implantable medical device 10, to be programmably stored and modified, as required, in order to customize the implantable medical device's operation to suit the needs of a particular patient. Such data includes basic timing intervals used during operation of the implantable medical device 10 for triggering of ventricular or atrial stimulation pulses.

Further, data sensed during the operation of the implantable medical device may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and some remote programming or analyzing device, which can be part of a centralized service center serving multiple implantable medical devices.

For impedance measurement, an impedance determination unit 70 is provided. Impedance determination unit 70 comprises a constant current source 72 that is connected or can be connected to electrodes for intracorporeal placement as shown in FIG. 1 to 3. In order to allow for a plurality of impedance measurement electrode configurations, preferably some means of switching is provided between the constant current source 72 and the electrode terminals of the implantable medical device 10. The switch is not shown in FIGS. 4 and 5. Rather, particular impedance measurement configurations are shown as examples.

Similarly, a measuring unit 74 for measuring a voltage corresponding to a current fed through a body by said constant current source is provided and can be connected to a number of electrodes as illustrated by table 1 (see above) although a switch for switching between these configurations is not shown in FIGS. 4 and 5.

As an alternative to constant current source 72 a constant voltage source can be provided. Then, the measuring unit will be adapted to measure a current strength of a current fed through a body by said constant voltage source.

Both, constant current source 72 and measuring unit 74, are connected to an impedance value determination unit 76 that is adapted to determine an impedance value for each measuring current pulse delivered by the constant current source 72.

Further, an impedance measuring control and evaluation unit 78 is provided, that is connected to said impedance determination unit and that is adapted to control said impedance determination unit and to evaluate a sequence of consecutive impedance values determined by said impedance determination unit. Impedance measuring control and evaluation unit 78 is also connected to memory 56 and to telemetry unit 58 to allow for storing of impedance data and further evaluation by an external service center.

The impedance determination unit 70 is adapted to determine at least intrathoracic impedance values and intracardiac impedance values for same period of time, wherein the intrathoracic impedance values are sampled with a lower sampling rate than the intracardiac impedance values.

Implantable medical device 10 usually comprises an activity sensor ACT 60 that is used for rate adaptation and can be of further use for evaluation of impedance values and therefore is connected to the impedance determination unit 70 via control unit CTRL 54.

In an uncomplicated scenario of progression into pulmonary edema or resorption of thoracic fluid, table 2 (see above) shows the hypotheses to test for the classification of thoracic fluid status change. In general, fluid exuding into the impedance path (pulmonary interstitium) or remaining in the impedance path (low ejection fraction) causes a drop in impedance. Some configurations may cause an increase in expected impedance with thoracic fluid secondary to heart failure if accompanied by enlargement of the ventricle and a distancing of the measurement leads. In all cases, an earlier or extrapolated reference value is compared to a more recent value to test for classification.

Figure 7:
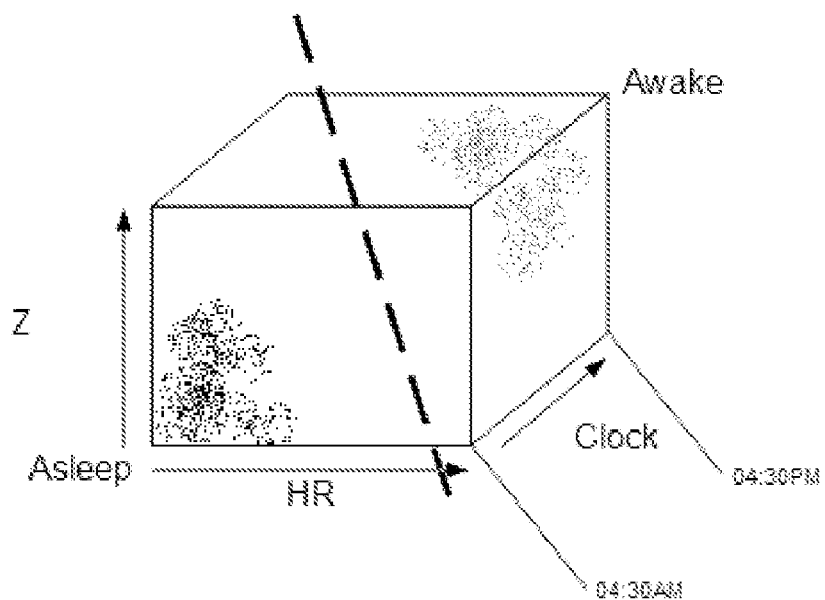
FIG. 7 is a graphical representation of clusters of points representing different alert or activity states, and by longer epochs infer the health state of a patient.

It is expected that the patient performs some level of activities of daily living. Therefore, there are changes in body position, fluid intake and excretion, activity versus rest cycles imposing an effect on the impedance measurements. Because of these, it is preferred that combinations of impedance measurements are part of routine monitoring, because the intrathoracic fluid will collect in the gravitationally dependent position. In fact, because of a preferred sleeping position, different configurations may not be confirmatory of each other. Hence, the use of additional indicators. FIG. 7 shows conceptually how three of the biological signals are brought together in one of many possible combinations to discriminate activity versus rest. In this scenario, decreased heart rate and the system clock time differentiate the variation in activity level and body position in one possible impedance measurement.

Figure 8:
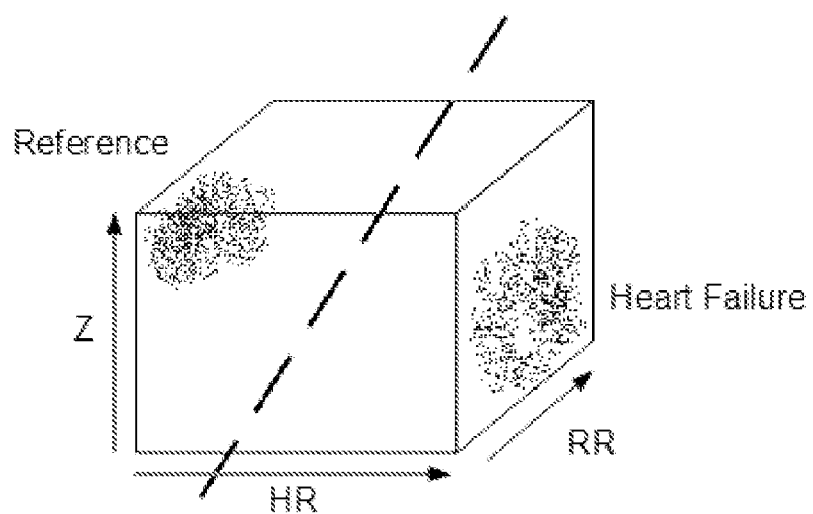
FIG. 8 is a further graphical representation of points of clusters representing health states of a patient.

Other signals that affect the impedance value are the cardiac contraction and respiration. Instead of filtering out these artifacts or gating to obviate their effects, they are used in this method to provide additional diagnostic information. In the case of respiration, consider FIG. 8 in which three of the biological signals are brought together in one of many possible combinations to discriminate a baseline physiologic state versus accumulated thoracic fluid associated with pulmonary edema. In the reference condition impedance, heart rate and respiratory rate are nominal (cluster of points in upper left). In the scenario that a heart failure causes pulmonary edema, values migrate to decreased impedance, and increased heart and respiratory rates (cluster of points in lower right rear of figure). The dashed line indicates the discriminant that minimizes the error between the classes: condition nominal and increased thoracic fluid.

Other available signals are used. For example, it is expected that respiration will correlate positively with activity sensor levels in health and inversely correlate in progressive primary pulmonary edema or secondary to CHF.

Figure 9:
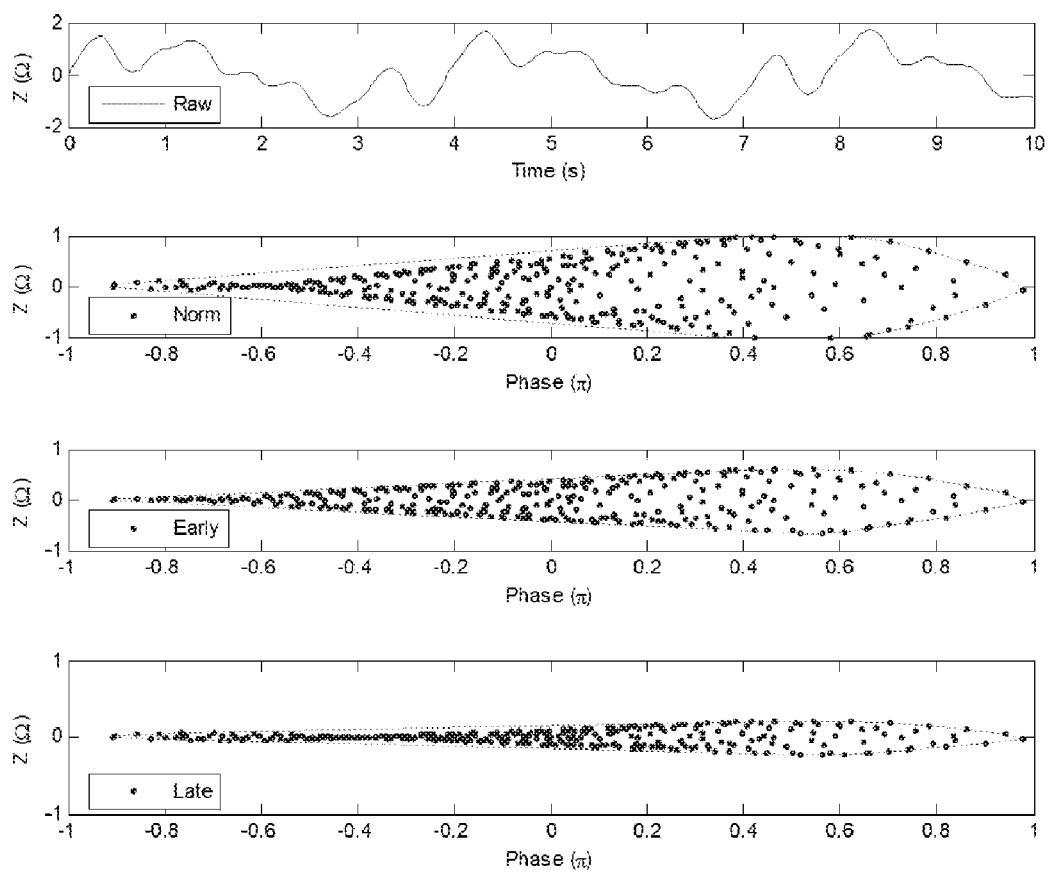
FIG. 9 is a representation of a typical time course of intrathoracic impedance together with three phase plots for different health states of a patient.

To reiterate, instead of discounting the cardiac and respiratory artifacts, they are in fact used to provide additional corroborating data for thoracic fluid accumulation. Consider the top graph labeled 'Raw' of FIG. 9, where an impedance waveform is modulated by both cardiac contraction and respiratory artifacts. The lower three graph (labelled 'Norm,' 'Early,' and 'Late') shows examples of changes to the modulation phase envelope of the impedance waveform associated with nominal, initial, and later stages of heart failure, respectively. The latter graphs are plotted in terms of Ohms of a fiducial value of $Z_{cardiac}$ versus the phase between a fiducial value of $Z_{resp}$ and a fiducial value of $Z_{cardiac}$. The primary observation is that modulation amplitudes decrease as heart failure progresses. This decrease is associated with a flattening of the Frank-Starling curve associated with heart failure. The effect may also be related also to the decreased stroke volume variance due to increased sympathetic tone (a compensatory response to heart failure). The method is immune the effect of the joint phenomenon of decreased magnitude of the pulmonary and cardiac components of the impedance signal due to thoracic fluid accumulation.

Figure 10:
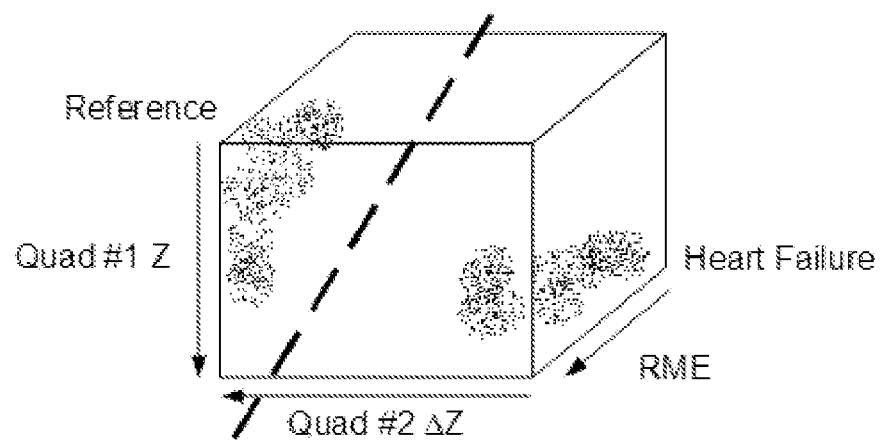
FIG. 10 is a further graphical representation of clusters of points combining impedance measurements and respiratory modulation envelope data as represented in FIG. 9.

The method also generates a respiration rate, tidal, and minute volumes, and modulation envelope and does not require gating or filtering the impedance measurement. The cardiac, respiratory, and other noise is not discounted from the signal, but rather used along with event information from the atrial or ventricular channels to identify fiducial points of respiration and cardiac contraction and their interactions (of which one is the modulation envelope). See FIG. 10, in which three of the biological signals are brought together in one of many possible combinations to discriminate a baseline physiologic state versus accumulated thoracic fluid associated with pulmonary edema (Quad#1 Z, Quad#2 ΔZ, and RME refer to the mean, and amplitude of the Quadrapolar Z measurement numbered in Table 1 and the area of the Respiratory Modulation Phase Envelope, respectively). In the figure, the arrows parallel to each axis indicate the direction of increasing values. In this scenario, the reference physiologic state is associated with good left ventricular emptying, greater cardiac dynamics, and larger respiration modulation envelope amplitude (upper left cluster of points). As a heart failure ensues that would cause pulmonary edema, more fluid is retained in the left ventricle at the end of systole, cardiac dynamics decrease, and the respiratory modulation envelope is attenuated (cluster of points in lower rear right of cube).

Figure 6:
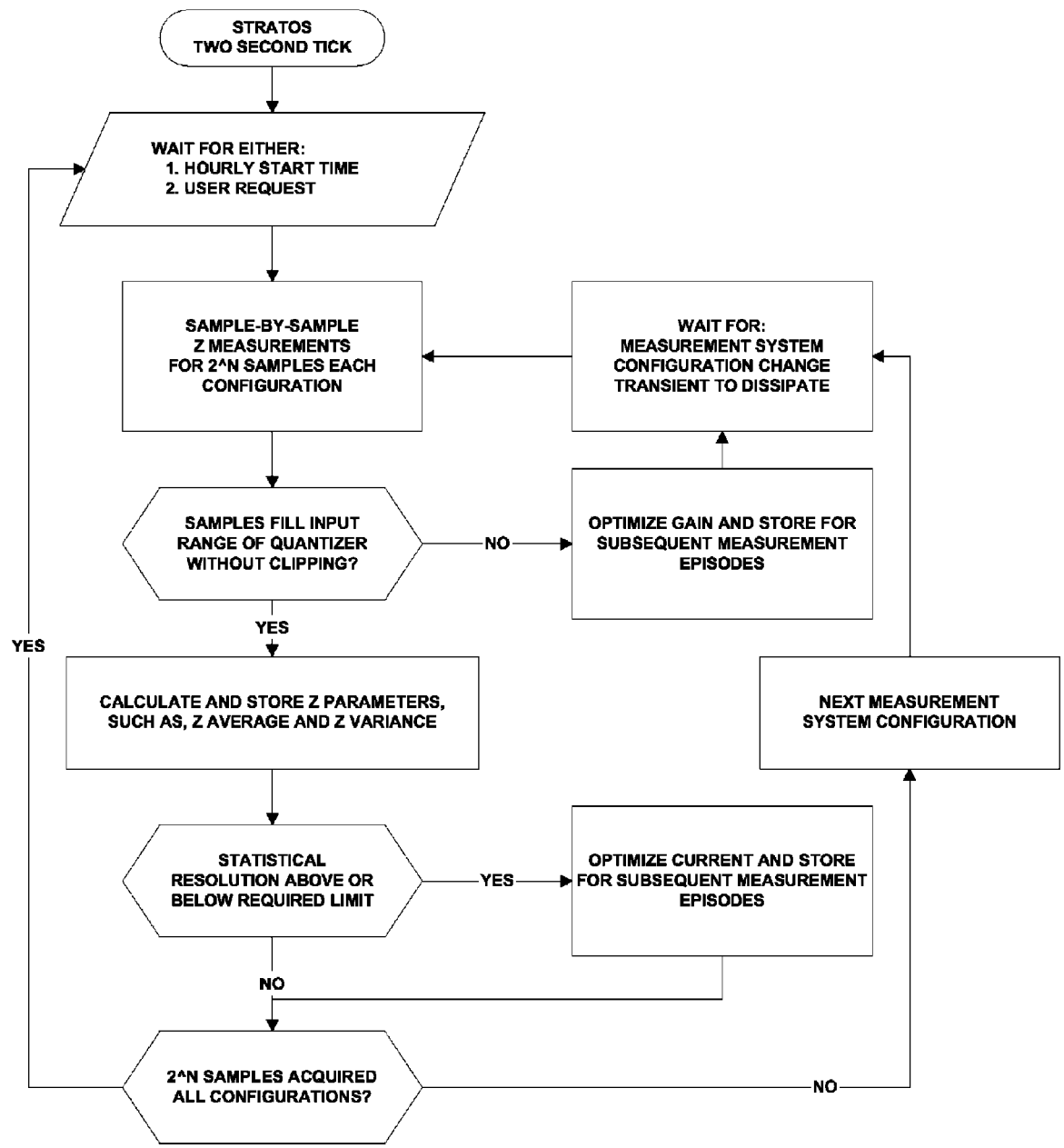
FIG. 6 is a flow chart of a preferred method according to the invention.

Details of the operation of the impedance determination unit 70 (FIGS. 4 and 5) as well as a method of evaluating impedance values are illustrated in FIG. 6.

FIG. 6 shows the scheduling logic for obtaining impedance measurements and the processing of the data. The impedance determination unit 70 is adapted to automatically adjust the measurement gains to accommodate values outside the operating range of the quantizer. The gain adjustment process is bidirectional, and can adapt to large and small signals. When the impedance signal is sampled various parameters based on its value can be calculated in the implantable medical device 10. Most notably, the variance is used to compute the resolution of the sample average (as opposed to the impedance measurement resolution). The forcing function is adjusted to make the resolution of the average value meet requirements for a test of statistical significance. Overflow restarts a measurement, whereas increases in gain or current are applied to the next measurement. Therefore, the impedance determination unit 70 always gathers data instead of aborting until the next scheduled measurement, but prevents oscillating between settings by means of this decision hysteresis.

Operationally, the impedance measurements are gated by a $2^N$ sample counter, or alternatively a $2^N$ second time window, and synchronously to measurement unit sample timing ticks. Sample values and paced or sensed event signals generated by implantable medical device timing and control unit CTRL 54 are passed to the fluid status monitor of impedance determination unit 70. Sampling, unsynchronized to the cardiac sensed or paced event, provides thoracic fluid measurement data decorrelated from the cardiac cycle and therefore more likely to sample more morphological details. Both the original time series of impedance measurement samples and values derived from it, may be stored in memory MEM 56 and transmitted via telemetry unit TEL 58 for further online or offline processing by home monitoring.

Furthermore, the intrathoracic impedance measurement is preferably performed throughout the time that the heart volume is changing. The changing blood volume of the heart contributes to the impedance measurement; therefore an impedance measurement is taken during all phases, systole and diastole. Because the impedance measurement is taken continuously, such morphological features as the rapid ejection phase of systole, the rapidly changing heart blood volume will add a desirable variation to the impedance measurement that is modulated by respiration. Additionally, other volumetric phases of the cardiac cycle are useful fiducial points for the analysis of stroke variation as an indicator of CHF and consequent lung edema.

The method is unconstrained in time in the sense that impedance measurements do not have to be restricted to a certain refractory part of the cardiac cycle to avoid capture, or a vulnerable period. Impedance measurement pulses are emitted below the strength duration curve in voltage and pulse width. A safety margin of at least two orders of magnitude is maintained at 0.5V and 15 microseconds. Additionally, because of the use of very low-energy bipolar current pulses, lead corrosion does not occur, device battery lifetime is not impacted, event gating is optional, and sampling rate does not have to be compromised.

The intrathoracic impedance measurements may or may not be respiration-gated. The respiration-gated measurements allow reduction of the number of impedance measurements to be performed. One intrathoracic impedance measurement episode may be performed per spanning whole respiration cycle(s) by starting and ending on the same respiration feature. If respiration-gated measurements are not performed, a higher count of impedance measurements would be required to dilute the bias in the average value caused by stopping in a partially completed respiration cycle.

In one embodiment, hourly fluid status 10 bit impedance values are summed in, for example, a 24 bit accumulator. At the conclusion of the measurement, the average is obtained by assigning the binary fixed point to the accumulated value (No division is necessary because the number of samples is $2^N$). In this example, the integer portion of the hourly fluid status impedance average can be stored in bits 15-6. The fractional portion of the hourly fluid status impedance average is then stored in bits 5 0 with bit 5 indicating 0.5 ohms when set and bit 4 indicating 0.25 ohms when set, and so on. In this way, the average value can have a computational resolution of 0.015625 Ohms. Because the variance is calculated like the average, the statistical resolution can be estimated due to the relation var/N and subsequently trigger changes to the current value to meet measurement resolution requirements.

The impedance measurement system (impedance determination unit 70) is capable of concurrent sampling of multiple impedance measurement electrode configurations. This may be accomplished either by analog configurations or digital configurations that are time multiplexed rapidly enough so that the sample rate per channel meets or exceeds the Nyquist criterion. Therefore, cross correlation between time domain features of the impedance waveform is possible.

Additionally, the impedance measurement system is capable of custom modifications of the excitation pulse duty cycle or sign. Therefore, the impedance measurement may alternate in a custom pattern between pulses of various widths and inter pulse delays to measure the impedance of different tissue types. By this method, discrimination between the impedances of visceral versus pleural, and vascular versus interstitial may be accomplished.

When low impedance pacing tip electrodes are available, such electrodes are preferred for intrathoracic impedance measurements. Due to the increased surface area typical of fractal pacing tip electrodes, the electrode-tissue interface impedance, when the tip electrode is included in the measurement pathway, makes a relatively small contribution to the intrathoracic impedance measurement, revealing small changes in impedance due to variations in tissue fluid content. When methods of the present invention are implemented in cardiac stimulation devices such as cardiac pacemakers, the ring electrode is preferred as the forcing function electrode for the excitation path and the tip electrode is used in the path measuring the response function.

In summary, the preferred features and advantages of the method and the device according to the invention from other or older methods and devices that should have been revealed by the foregoing description are:

The method and the device combine inputs previously rejected by prior art or inputs not directly available in an implant (but synthesized from inputs) to classify the patient condition as changed in thoracic fluid status.

The method and the device make thoracic fluid status assessments hourly instead of once per day.

The method does not require limiting the measurement window to a certain part of the cardiac cycle.

The method and the device vary the measurement current pulse width to differentiate tissue from fluid.

The method and the device monitor for signs of heart failure to generate an indicator for impending or resolving thoracic fluid.

The method uses secondary indicators to modify the confidence of a primary indicator.

The method and the device provide for the possibility to employ numerous additional new measurement configurations.

Neither the method nor the device require a coil as a lead contact element in the measurement configuration.

The method and the device use combinations of configurations for discriminating a primary pulmonary edema from one secondary to heart failure.

The method and the device use combinations of measurements to test the hypothesis that a classification change in thoracic fluid status has occurred.

The method and the device employ some unique configurations to indicate cardiac function, including one that is expected to increase in value as a prodromal sign of increased thoracic fluid.

The method and the device recognize gravitational dependence of edema due to positions and compensates.

The method and the device combine the system clock, accelerometer (activity sensor output), heart rate, impedances at different time offsets, and diurnal variations to detect and compensate for circadian variations in measurements.

The method and the device use the discriminant between classes of multiple values minimizing the classification error.

The method and the device do not require filtering or gating to remove cardiac or respiratory artifacts.

The method and the device use cardiac or respiratory artifacts in a unique way to provide additional confirmatory data.

The method and the device use respiratory modulation of the stroke artifact to infer cardiac status and impending pulmonary edema.

In general, the invention provides for a method of monitoring intrathoracic fluid content, comprising:
measuring intrathoracic impedance between a first electrode and a second electrode continuously without regard to the cardiac cycle, achieving reduced amount of electrical noise due to filtering, averaging, and auto gain and auto current magnitude methods and providing an impedance output signal thereof;
a method making it unnecessary to perform additional noise removal from the impedance output signal;
storing the un-filtered impedance output signal;
performing steps for a predetermined number of measurement unit sample timing ticks to thereby generate a set of un-filtered impedance data; and
mathematically manipulating the sample of impedance data to render an estimate of population statistics from said sample of impedance data.

Because the monitoring performed by the device corresponding to the method is a continually sampled waveform, it includes all and non limited to the following: intrinsic refractory period, isovolumetric contraction, end-diastolic point, valve opening, peak systolic phase, valve closing, and isovolumetric relaxation.

The continuous impedance measurement can be temporarily discontinued for a predetermined interval after delivery of the pacing pulse to a cardiac chamber comprising an interval of between 15 and 130 milliseconds in 7.8 ms steps.

The device employs a pulse of energy that is monophasic alternating in sign.

The device adjusts the pulse of energy current level until the measurement properties satisfy a required resolution.

The method and the device do not require that the pulse of energy voltage level be predetermined.

The method detects invalid samples due to invalid quantizer states, overflow, underflow, pacing artifact and replaces the value with zero order, first order, or second order extension of other known values into the memory location of the invalid sample.

It is not required that the method and the device filter the impedance signal, because the indicative parameters would be obscured and are rather separated mathematically.

The first electrode may be a case, coil, ring, or tip electrode of an ICD lead, pacemaker bipolar or unipolar or other implantable medical device electrode.

The first, second, third, and fourth electrodes may be located in the right or left ventricle, left ventricular vein, epicardium, sub clavicular or pectoral pocket.

The only requirement is that the axes of the electrode pairs pass through a section of the lung for the measurement to detect primary lung edema, and pass through the ventricles of the heart for the measurement to detect secondary lung edema.

The method is performed at least hourly and provides indications of statistically significant changes in thoracic impedance.

The method displays trends of likelihood of lung edema and discriminatory power of elapsed measurements.

The device comprises a disabling circuit for sensing during the measurement pulse.

The method and the device do not require a predetermined value to compare stored lead impedance values and prior lead impedance for rejection. Rather, the method and the device accept all measurements to build the distributions of reference, successive, and recent epochs of lead impedances for significance testing.

By partitioning the data according to the 12 to 24 hour duration, the method and the device use a combination of respiration, heart rate, and accelerometer to identify the diurnal variation in impedance.

By partitioning the data according to longer epochs, the method and the device use a combination of respiration, heart rate, and accelerometer to identify the trends in impedance that identify physiologic decompensation because of or recovery from lung edema primary or secondary to heart failure.

The method decomposes the Z waveform into components $Z_{thoracic}$ and $Z_{cardiac}$.

The method establishes the amplitude modulation envelope due to respiration versus the phase difference of $Z_{thoracic}$ and $Z_{cardiac}$.

The method considers the diurnal variation and makes determinations based on longer epochs.

The device applies high-pass, low-pass and band-pass filters at adjustable frequencies, or other combinations of filtering or recursively to reveal Z waveform signal components capable of revealing the state of primary or secondary lung edema.

The method and device provide a means by which the signal is synchronously time averaged on a fiducial point of the EGM, Accelerometer, Z waveform, or any derived signal over hourly, daily, and longer epochs. Statistical moments of the resulting morphological features contribute to classification.

The method and device require no patient interaction, but rather is capable of outbound or two-way communication with the Home Monitoring Center to inform of present status or changes in the primary or secondary indicators of lung edema.

The method and device provide a means for storing the compressed or raw impedance output signal.

The method and device provide a means for storing the statistical moments of the impedance output signal.

The method and device provide a means of arithmetically combining simultaneous measurements so that the filling and emptying phase relationships between chambers can be established providing an indicator for hemodynamics producing secondary pulmonary edema.

The method and device provide a means for calibrating the system against a Z reference.

The method and device provide a means to discriminate thoracic fluid accumulation due to pulmonary edema versus pericardial effusion in, for example, transplant rejection.

Although an exemplary embodiment of the present invention has been shown and described, it should be apparent to those of ordinary skill that a number of changes and modifications to the invention may be made without departing from the spirit and scope of the invention. In particular, it is possible to implement the features of the claimed transceiver unit into state of the art implantable medical devices such as implantable pacemakers or implantable cardioverter/defibrillator. Further, it is possible to chose other electrode configurations for impedance determination based on the electrode configurations available for a particular device. This invention can readily be adapted to such devices by following the present teachings. All such changes, modifications and alterations should therefore be recognized as falling within the scope of the present invention.

What is claimed is:

1. An implantable medical device comprising:
    an impedance determination unit comprising
        a constant current source or a constant voltage source having current feed terminals that are connected or can be connected to electrodes for intracorporal placement and that is configured to generate measuring current pulses having a constant current strength or a constant voltage, respectively, to cause a current to be fed through a body via intracorporally placed electrodes;
        a measuring unit configured to measure a voltage corresponding to a current fed through a body by said constant current source or a current strength of a current fed through a body by said constant voltage source, respectively;
        an impedance value determination unit that is connected to said constant current source or said constant voltage source and to the measuring unit wherein said impedance value determination unit is configured to determine an impedance value for each measuring current pulse; and,
    an impedance measuring control and evaluation unit, that is connected to said impedance determination unit and that is configured to control said impedance determination unit and to evaluate a sequence of consecutive impedance values determined by said impedance determination unit; and
    said impedance determination unit further configured to determine at least intrathoracic impedance values and intracardiac impedance values concurrently, wherein the intrathoracic impedance values are sampled with a lower sampling rate than the intracardiac impedance values, determine respiration rate values from said intrathoracic impedance values, determine heart rate values from said intracardiac impedance values, evaluate said sequence of consecutive impedance values based on said respiration rate values and said heart rate values.

2. The implantable medical device according to claim 1, wherein the impedance determination unit is further configured to determine at least two kinds of intrathoracic impedance values comprising:

a first kind corresponding to an impedance between an IMD case and at least one electrode to be placed in one ventricle of a heart; and, a second kind corresponding to an impedance between an IMD case at least one intracardiac electrode.

3. The implantable medical device according to claim 1, wherein the impedance determination unit is further configured to determine at least two kinds of intrathoracic impedance values comprising:

a first kind corresponding to an impedance between an IMD case and an electrode to be placed in a right ventricle of a heart, and a second kind corresponding to an impedance between an IMD case and an electrode to be placed in a left ventricle of a heart.

4. The implantable medical device according to claim 2 wherein the impedance determination unit is further configured to determine said intrathoracic impedance values wherein:

said constant current source is connected to the IMD case and a right ventricular or a left ventricular ring electrode, respectively, such that a current pulse injection source is the respective ring electrode and the current pulse sink is the IMD case; and, wherein said impedance determination unit measures a voltage between the IMD case and a right ventricular or a left ventricular tip electrode, respectively.

5. The implantable medical device according to claim 1, wherein the impedance determination unit is further configured to determine said intracardiac impedance values to be an impedance between an electrode in a right ventricle of a heart and an electrode in a left ventricle of a heart.

6. The implantable medical device according to claim 5, wherein the impedance determination unit is further configured to determine said intracardiac impedance values wherein:

said impedance determination unit is connected via the constant current source to a right ventricular ring electrode and a right ventricular tip electrode, such that a current pulse injection source is the right ventricular ring electrode and the current pulse sink is the right ventricular tip electrode; and, wherein said impedance determination unit measures a voltage between a left ventricular ring electrode and a left ventricular tip electrode.

7. The implantable medical device according to claim 1, wherein the impedance determination unit comprises a quantizer having an operating range and wherein the impedance determination unit is configured to automatically adjust measurement gains of an amplifier to accommodate values outside the operating range of said quantizer.

8. The implantable medical device according to claim 7, wherein the impedance determination unit is further configured to perform a bidirectional gain adjustment process that can adapt to large and small signals.

9. The implantable medical device according to claim 8, wherein the impedance determination unit is further configured to use variance to compute a resolution of a sample average and to adjust a forcing function to make a resolution of an average value meet requirements for a test of statistical significance.

10. The implantable medical device according to claim 1, wherein the impedance determination unit is further configured to measure a $Z_{cardiac}$ waveform from an atrial lead and to use said $Z_{cardiac}$ waveform to verify the atrial contribution to cardiac output as an indicator of overall cardiac output.

11. The implantable medical device according to claim 1, wherein the implantable medical device comprises an activity sensor that is connected to said impedance measuring control and evaluation unit and wherein said impedance measuring control and evaluation unit is configured to process an output value generated by said activity sensor for evaluating said sequence of consecutive impedance values.

12. The implantable medical device according to claim 1, wherein the implantable medical device comprises sensing means configured to sense electric potential indicating excitation of myocardium and a heart rate detector connected to said sensing means to determine a heart rate, wherein said impedance measuring control and evaluation unit is connected to said heart rate detector and is configured to use heart rate values received from said heart rate detector to evaluate said sequence of consecutive impedance values.

13. The implantable medical device according to claim 1, wherein said impedance measuring control and evaluation unit is configured to perform a population analysis based on sequences of consecutive impedance values.

14. The implantable medical device according to claim 1, wherein said impedance measuring control and evaluation unit is configured to determine predetermined population properties through analysis of a cluster of points in at least three-dimensional space wherein a first dimension is given by a heart rate and a second dimension is given by an impedance and the third dimension is either a time of day or a respiratory rate and wherein each point of said cluster is determined by a triplet formed by a heart rate value, an impedance value and either a time of day value or a respiratory rate value.

15. The implantable medical device according to claim 2, wherein said impedance measuring control and evaluation unit is configured to compare a recent intrathoracic impedance value to a reference intrathoracic impedance value and to detect a decrease in thoracic fluid if said recent intrathoracic impedance value exceeds said reference intrathoracic impedance value.

16. The implantable medical device according to claim 2, wherein said impedance measuring control and evaluation unit is configured to compare a recent intrathoracic impedance value to a reference intrathoracic impedance value and to detect a change in thoracic fluid if said recent intrathoracic impedance value shows a corresponding change in said reference intrathoracic impedance value.

17. The implantable medical device according to claim 5, wherein said impedance measuring control and evaluation unit is configured to compare a recent intracardiac impedance value to a reference intracardiac impedance value and to detect a change in end-systolic volume if said recent intracardiac impedance value shows a corresponding change in said reference intracardiac impedance value.

18. The implantable medical device according to claim 5, wherein said impedance measuring control and evaluation unit is configured to compare a recent intracardiac impedance value to a reference intracardiac impedance value and to detect an increase in end-systolic volume if said recent intracardiac impedance value is smaller than said reference intracardiac impedance value.

19. The implantable medical device according to claim 1, wherein said impedance measuring control and evaluation unit is configured to analyse a modulation of a fiducial value in said intracardiac impedance $Z_{cardiac}$ by said intrathoracic impedance $Z_{resp}$ that corresponds to a cardiac function indication of a Frank-Starling curve, and determine absence, decompensation to, presence of, or resolution from heart failure as a prodromal or other confirmatory sign of lung edema.

20. The implantable medical device according to claim 19, wherein said impedance measuring control and evaluation unit is configured to determine a fiducial value of $Z_{cardiac}$ versus a phase between a fiducial value of $Z_{resp}$ and a fiducial value of $Z_{cardiac}$.

21. The implantable medical device according to claim 19, wherein said impedance measuring control and evaluation unit is configured to detect a significant decrease in modulation amplitudes in a graph representing said fiducial value of $Z_{cardiac}$ versus said phase between said fiducial value of $Z_{resp}$ and said fiducial value of $Z_{cardiac}$.

22. The implantable medical device according to claim 1, wherein said constant current source is further configured to generate monophasic measuring current pulse and to alternate polarity of the measuring current pulses from current pulse to current pulse.

23. The implantable medical device according to claim 1, wherein the impedance determination unit is further configured to vary a measurement pulse duration from pulse to pulse.

24. The implantable medical device according to claim 1, wherein said constant current source is further configured to generate measuring current pulse having a pulse strength that is smaller than an excitation threshold of a myocardium.

25. The implantable medical device according to claim 1, wherein the impedance determination unit is further configured to modulate a sampling rate for intrathoracic impedance samples such that the sampling rate is not constant but varies about 10% or less.

26. The implantable medical device according to claim 1, wherein the impedance determination unit is further configured to limit each sequence of impedance values to represent a single full respiratory cycle.

27. The implantable medical device according to claim 1, wherein the impedance determination unit is further configured to initiate recording of a sequence of impedance values several times a day.

28. The implantable medical device according to claim 1, wherein the impedance determination unit is further configured to initiate recording of a sequence of impedance values once an hour.

29. The implantable medical device according to claim 1, wherein the impedance determination unit comprises a switch matrix that is arranged between said constant current or constant voltage source and said measuring unit on one side and said electrodes on the other side and wherein the impedance determination unit is further configured to alternate an electrode configuration from time to time by controlling said switch matrix such that connections between said constant current or constant voltage source and said measuring unit on one side and said electrodes on the other side are altered.

30. An implantable medical device comprising:
an impedance determination unit comprising
a constant current source or a constant voltage source having current feed terminals that are connected or can be connected to electrodes for intracorporal placement and that is configured to generate measuring current pulses having a constant current strength or a constant voltage, respectively, to cause a current to be fed through a body via intracorporally placed electrodes;
a measuring unit configured to measure a voltage corresponding to a current fed through a body by said constant current source or a current strength of a current fed through a body by said constant voltage source, respectively;
an impedance value determination unit that is connected to said constant current source or said constant voltage source and to the measuring unit wherein said impedance value determination unit is configured to determine an impedance value for each measuring current pulse; and,
an impedance measuring control and evaluation unit, that is connected to said impedance determination unit and that is configured to control said impedance determination unit and to evaluate a sequence of consecutive impedance values determined by said impedance determination unit;
said impedance determination unit further configured to determine at least intrathoracic impedance values and intracardiac impedance values concurrently, wherein the intrathoracic impedance values are sampled with a lower sampling rate than the intracardiac impedance values;
said impedance measuring control and evaluation unit further configured to
determine a respiratory rate from said intrathoracic impedance values and to use respiration rate values thus determined to further evaluate said sequence of consecutive impedance values;
determine a heart rate from said intracardiac impedance values and to use heart rate values thus determined to further evaluate said sequence of consecutive impedance values;
perform a population analysis based on said sequences of consecutive impedance values and
determine population properties through analysis of a cluster of points in at least a three-dimensional space wherein a first dimension is given by a heart rate and a second dimension is given by an impedance and a third dimension is either a time of day or a respiratory rate and wherein each point of said cluster is determined by a triplet formed by a heart rate value, an impedance value and either a time of day value or a respiratory rate value.

31. An implantable medical device comprising:
an impedance determination unit comprising
a constant current source or a constant voltage source having current feed terminals that are connected or can be connected to electrodes for intracorporal placement and that is configured to generate measuring current pulses having a constant current strength or a constant voltage, respectively, to cause a current to be fed through a body via intracorporally placed electrodes;
a measuring unit configured to measure a voltage corresponding to a current fed through a body by said constant current source or a current strength of a current fed through a body by said constant voltage source, respectively;

an impedance value determination unit that is connected to said constant current source or said constant voltage source and to the measuring unit wherein said impedance value determination unit is configured to determine an impedance value for each measuring current pulse; and, an impedance measuring control and evaluation unit, that is connected to said impedance determination unit and that is configured to control said impedance determination unit and to evaluate a sequence of consecutive impedance values determined by said impedance determination unit;

said impedance determination unit further configured to determine at least intrathoracic impedance values and intracardiac impedance values concurrently, wherein the intrathoracic impedance values are sampled with a lower sampling rate than the intracardiac impedance values;

said impedance measuring control and evaluation unit further configured to compare a recent intrathoracic impedance value to a reference intrathoracic impedance value and to detect a decrease in thoracic fluid if said recent intrathoracic impedance value exceeds said reference intrathoracic impedance value, and compare a recent intrathoracic impedance value to a reference intrathoracic impedance value and to detect a change in thoracic fluid if said recent intrathoracic impedance value shows a corresponding change in said reference intrathoracic impedance value, and compare a recent intracardiac impedance value to a reference intracardiac impedance value and to detect a change in end-systolic volume if said recent intracardiac impedance value shows a corresponding change in said reference intracardiac impedance value, and compare a recent intracardiac impedance value to a reference intracardiac impedance value and to detect an increase in end-systolic volume if said recent intracardiac impedance value is smaller than said reference intracardiac impedance value, and analyse a modulation of a fiducial value in said intracardiac impedance $Z_{cardiac}$ by said intrathoracic impedance $Z_{resp}$ that corresponds to a cardiac function indication of a Frank-Starling curve, and determine absence, decompensation to, presence of, or resolution from heart failure as a prodromal or other confirmatory sign of lung edema.

* * * * *